United States Patent [19]

Kuyumciyan

[11] Patent Number: 5,471,998
[45] Date of Patent: Dec. 5, 1995

[54] CONDOM APPLICATOR

[76] Inventor: Levon Kuyumciyan, 34 Prince Phillip Avenue, Outremont, Quebec, Canada, H2V 2E8

[21] Appl. No.: 172,898
[22] Filed: Dec. 27, 1993
[51] Int. Cl.⁶ ...................................................... A61F 6/02
[52] U.S. Cl. ........................... 128/842; 128/844; 128/918
[58] Field of Search ...................................... 128/842, 844, 128/918; 604/330, 347–353

[56] References Cited

U.S. PATENT DOCUMENTS

| 2,567,926 | 9/1951 | Dunkelberger | 128/844 |
| 4,840,187 | 6/1989 | Brazier | 128/844 |
| 4,961,734 | 10/1990 | Kassman | 604/349 |
| 4,984,582 | 1/1991 | Romaniszyn et al. | 128/844 |
| 5,046,489 | 9/1991 | Gibson | 128/844 |
| 5,205,298 | 4/1993 | Hurst | 128/844 |
| 5,238,103 | 8/1993 | Swisher | 128/844 |
| 5,267,575 | 12/1993 | Hrisko | 128/844 |

Primary Examiner—Michael A. Brown
Attorney, Agent, or Firm—Foley & Lardner

[57] ABSTRACT

A condom holder for use in applying a condom onto a penis. The holder comprises a tubular member having a closed end and an open end. The tubular member is sized to very loosely cover the upper half of an erect penis. Mounting means are provided on the outside of the member adjacent its open end for mounting the open end of a condom thereon with an unrolled portion of the condom located within the member. An air opening is provided in the closed end of the condom to allow the passage of air between a space, formed between the unrolled portion of the condom and the interior surface of the member, and the atmosphere. Closure means are provided on the member for selectively closing the air opening. The closure means can be in the form of a valve or a frangible or removable seal. In use, with the condom mounted on the mounting means on the tubular member and with an unrolled portion of the condom located within the member, air is withdrawn from within the space between the holder and the condom through the air opening to cause the unrolled portion to stretch and enlarge. The air opening is then closed.

11 Claims, 3 Drawing Sheets

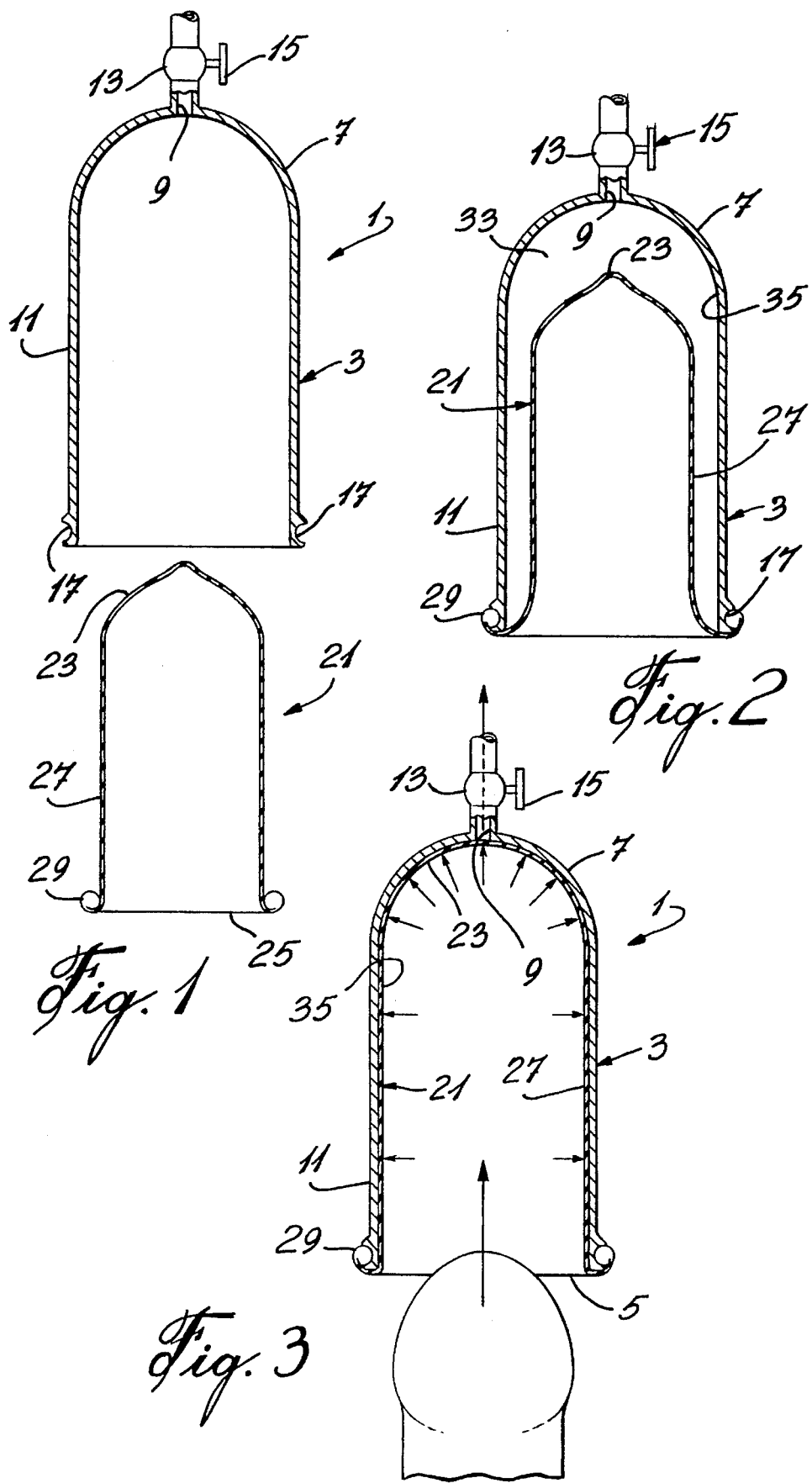

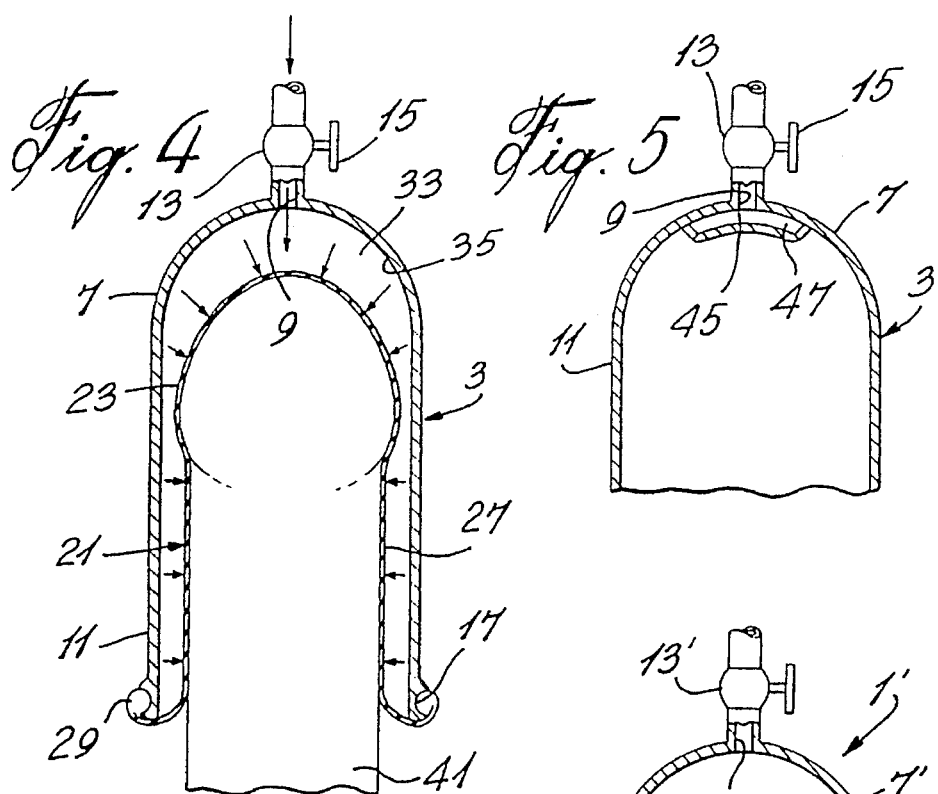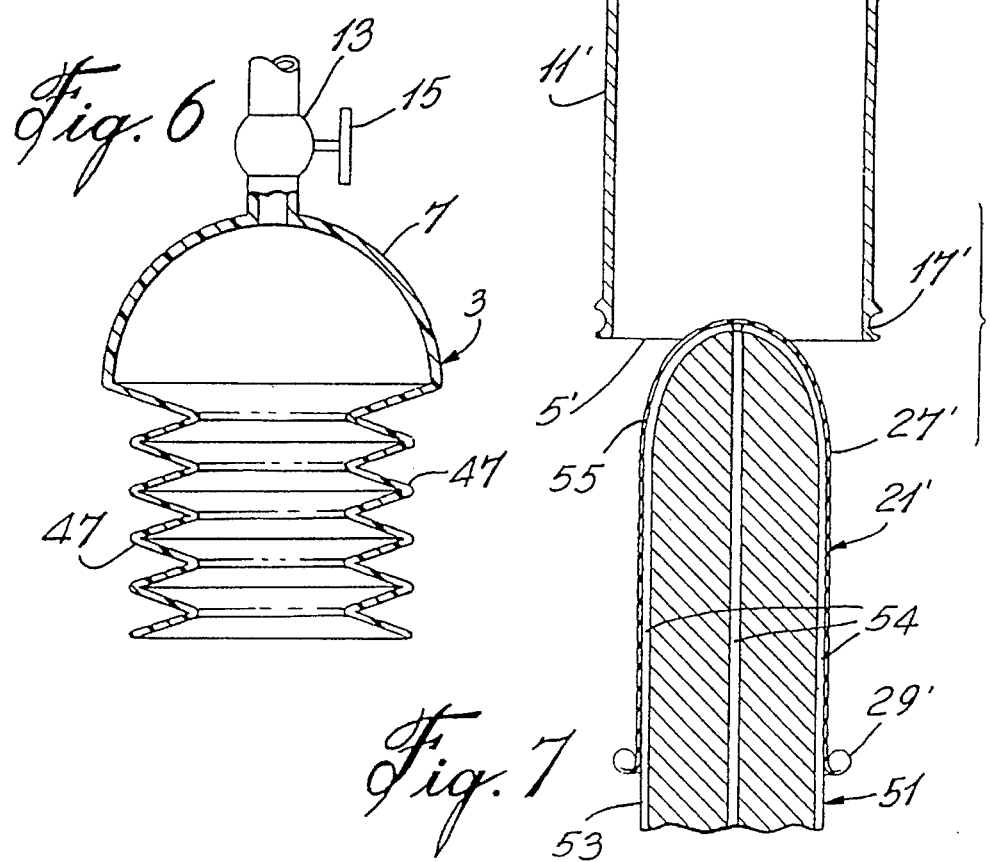

CONDOM APPLICATOR

BACKGROUND OF THE INVENTION

1. Field of the Invention

This invention is directed toward a holder for use in applying a condom. The invention is also directed toward a condom unit comprising the holder and a mounted condom. The invention is further directed toward a method of using the holder and the condom unit.

2. Description of the Prior Art

Applying a condom manually can be a difficult operation particularly because of the elasticity of the condom. It is known to provide holders for use in applying condoms which can be manipulated to stretch the condom to enlarge it, so as to make it easier to apply the condom. Examples of such holders are shown in U.S. Pat. Nos. 4,961,734, issued Oct. 9, 1990 to Kassman; and 5,205,298, issued Apr. 27, 1993 to Hurst. These known holders employ a generally tubular member on which the condom is mounted. The condom extends into the member. The member is extended while the condom is mounted thereon to reduce the pressure on the outside of the condom within the member. The atmosphere, acting on the inside of the condom, stretches and enlarges it within the member. The holder is then manipulated to position the stretched condom on the penis. When properly positioned, air is admitted into the holder to allow the stretched condom to collapse onto the penis and the condom is detached from the holder.

These known holders have various drawbacks, however. U.S. Pat. No. 4,961,734 employs a pleated holder. Expansion of the pleated holder creates reduced pressure within the holder so as to stretch the condom that is mounted thereon. However, this holder employs no valve means to relieve the pressure to collapse the condom. The condom is simply detached from the base end of the holder to collapse it. Thus, the condom collapses from the base outwardly towards its closed end, and an unwanted air bubble may form at the closed end of the condom when application is completed.

U.S. Pat. No. 5,205,298 discloses a pleated holder that admits air to collapse a stretched condom from the closed end of the condom toward the base. Thus, the possibility of an air bubble at the closed end of the condom is avoided. The holder has an air opening at its closed end. This opening is meant to be closed with the condom user's finger while the holder is extended so as to reduce pressure within the holder. Extension of the holder causes a condom mounted on the holder to stretch and enlarge. Once the condom is positioned on the penis, the finger is removed to collapse the condom from its closed end towards its base. An air bubble is avoided. However, it is difficult to keep the air opening sealed with a finger while manipulating the holder to stretch the condom and to position it. Several attempts may have to be made before the condom is sufficiently stretched and positioned so that it can be easily applied.

It is also known to provide rigid holders in which the condom is stretched by evacuating air mechanically from the holder. The condom and the holder form a condom unit which is sold with the condom already in the stretched condition. At the point of use, air is admitted into the holder to collapse the condom onto the penis. U.S. Pat. No. 4,984,582, issued Jan. 15, 1991 to Romaniszyn et al, discloses such a holder. However, the air control valve in the holder is located near the base of the condom. When the valve is opened to admit air to collapse the condom on the penis, the condom is collapsed from the base outwardly toward its closed end. This can result in an unwanted air bubble at the closed end of the condom when application is completed. In addition, the holder employs a double wall making it expensive.

SUMMARY OF THE INVENTION

It is a purpose of applicant's invention to provide a condom holder that is simple and inexpensive in construction.

It is another purpose to provide a condom holder constructed to avoid air bubbles when donning the condom.

It is a further purpose of applicant's invention to provide a condom holder that is efficient to use.

Applicant's condom holder comprises a tubular member having an open end and a closed end. Condom mounting means are provided on the outside of the member adjacent its open end. An air opening is provided in the closed end. Closure means are provided on the member for selectively closing the air opening. The use of selectively operable closure means allows the condom to be quickly and easily stretched, to be easily maintained in the stretched condition until positioned for application, and then to be simply collapsed.

In using the holder, the condom is partially unrolled with the unrolled portion of the condom inserted into the holder from the open end of the holder and with the rolled portion of the condom placed on the mounting means of the holder adjacent the open end. Air is then withdrawn from the space between the holder and the unrolled portion of the condom through the air opening in the closed end of the holder. This causes the unrolled portion of the condom to stretch and enlarge until it abuts the inner surface of the holder. The air opening is then closed by the closure means. When it is desired to don the condom, the holder is easily manipulated to position the unrolled stretched portion of the condom over the penis. When the condom is positioned, the closure means are operated to open the air opening allowing the unrolled portion of the condom to collapse onto the penis. The condom collapses from its closed end toward its open end. The rolled portion of the condom is detached from the holder, the holder is removed, and the rolled portion is manually unrolled onto the penis to complete donning of the condom.

In one embodiment of the invention, the air opening closure means can comprise a removable or breakable seal that is installed after the condom has been mounted onto the holder and stretched and enlarged by evacuating air. The seal is usually installed at the place of manufacture of the holder. The holder and installed condom are then packaged and sold as a condom unit. In this embodiment, it is contemplated that the holder is used only once. It is preferred that the holder is pleated. This allows the holder to be collapsed prior to packaging to save packaging costs. During use, the unit is unpackaged and pulled out to its original, uncollapsed shape prior to positioning the holder on a penis. Once the holder, and thus the stretched condom, is in position, the seal is removed or broken and the condom collapses onto the penis. The condom is then detached from the holder and the holder is discarded.

In another embodiment of the invention, the air opening closing means can comprise a permanently installed valve on the holder. In this embodiment, the holder can be sold with or without a condom and can be used many times with a fresh condom each time. The holder is used by mounting the condom onto the holder as before and then operating the valve to open the air opening. The user's mouth is then used to suck air through the air opening out of the space between the inner surface of the holder and the unrolled portion of the condom to stretch the unrolled portion of the condom. When the condom has been stretched, the valve is closed. After the holder is positioned relative to a penis, the valve is opened to allow the condom to collapse onto the penis. The holder can be pleated if desired so it can be collapsed and packaged and stored in a smaller space.

In both embodiments, air is drawn out of the air opening to reduce the pressure within the space between the unrolled portion of the condom and the inner surface of the holder. This can cause the closed end of the condom to block the air opening before sufficient air is removed to stretch the condom the desired amount. To avoid blockage, it is preferred that a shield is provided within the holder overlying the air opening. The shield is slightly spaced from the inner surface of the holder, and passageways allow air to pass around the shield and out the opening.

The invention is particularly directed toward a condom holder for use in applying a condom onto a penis. The holder comprises a single-walled, tubular member having a closed end and an open end, the member sized to very loosely cover the upper half of an erect penis. Mounting means are provided on the outside of the member adjacent its open end on which the open end of a partially unrolled condom is to be mounted with the unrolled portion of the condom located within the member. An air opening is provided in the closed end of the member to allow the passage of air between a space, formed between the unrolled portion of a mounted condom and the inner surface of the member, and the atmosphere. Closure means are provided on the member for selectively closing the air opening.

The invention is also directed toward a condom unit comprising a condom and a single-walled, tubular member having a closed end and an open end, the member sized to very loosely cover the upper half of an erect penis. Mounting means are provided on the outside of the member adjacent its open end on which the open end of the condom, which is partially unrolled, is mounted with the unrolled portion of the condom located within the member. An air opening is provided in the closed end of the member to allow the passage of air between a space, formed between the unrolled portion of the mounted condom and the inner surface of the member, and the atmosphere. Closure means are provided on the member for selectively closing the air opening.

The invention is further particularly directed toward a method of using the holder comprising the steps of mounting a partially unrolled condom, by its open end, on the mounting means at the open end of the holder with the unrolled portion of the condom located within the holder. Air is then evacuated from within the holder through the air opening in the closed end of the holder to stretch and enlarge the unrolled portion of the condom. After the condom has been enlarged, the air opening is closed by the closure means. The holder is then manipulated to position the stretched condom onto a penis. When the condom is in position, the closure means is operated to open the air opening which allows the unrolled portion of the condom to collapse onto the penis. The holder is then detached from the condom and removed.

BRIEF DESCRIPTION OF THE DRAWINGS

The invention will now be described in detail having reference to the accompanying drawings, in which:

FIG. 1 is an elevation view of the holder and a condom with the holder in cross-section;

FIG. 2 is an elevation view with the condom inserted into the holder with the holder in cross-section;

FIG. 3 is an elevation view, similar to FIG. 2, showing air being evacuated from the holder;

FIG. 4 is an elevation view showing the condom mounted on the holder and the holder positioned over a penis;

FIG. 5 is a detail view of the shield employed in the closed end of the holder;

FIG. 6 shows a collapsible holder;

FIG. 7 is an elevation view of a modified holder and an adapter used in mounting the condom;

DESCRIPTION OF THE PREFERRED EMBODIMENTS

Figure 8:
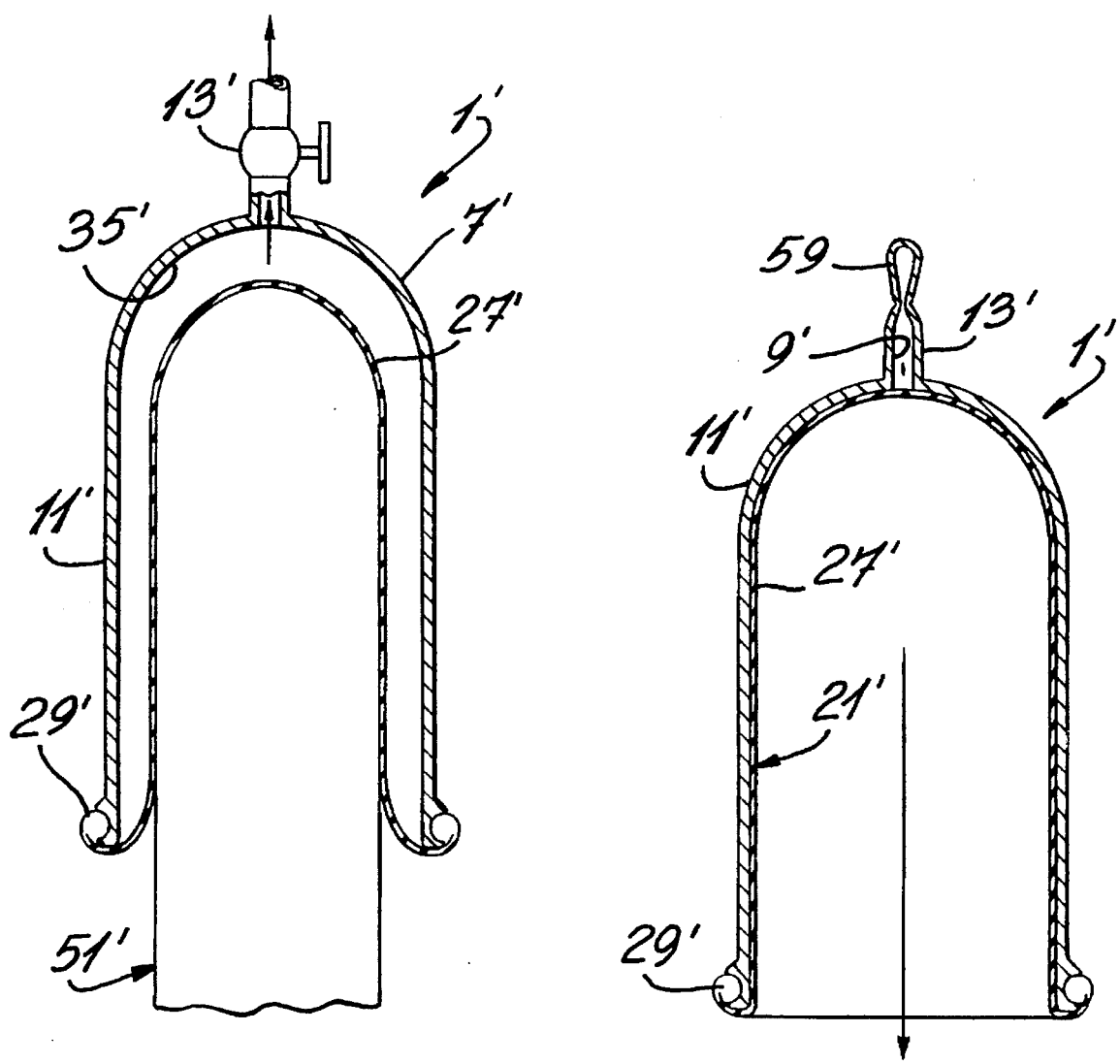
FIG. 8 is a view, similar to FIG. 7, showing the adapter inside the holder.

The holder 1 as shown in FIG. 1 comprises a single-walled tubular member 3 having an open end 5 and a rounded closed end 7. The tubular member 3 has a diameter approximately 4.5 to 5 cm. which is larger than an average erect penis and a length of about 12 cm. However, different sizes will be necessary, as there are presently different sizes of condoms. An air opening 9 is provided in the wall 11 of the member in the center of the closed end 7 leading through a short, small, tubular extension 13. Closure means in the form of a valve 15 are provided in the extension 13. Mounting means are provided adjacent the open end 5 of the member. The mounting means can comprise a circular channel or groove 17 formed in the outer surface of the wall 11 of the member 3 adjacent the open end 5.

A condom 21 is shown in FIG. 1. The condom 21 has a closed end 23 and an open end 25. The condom 21 is partially unrolled to provide a flaccid, unrolled portion 27. The remainder 29 of the condom 21 is rolled about a ring (not shown) at the open end 25 of the condom 21.

To mount the condom 21 on the holder 1, the unrolled portion 27 of the condom is inserted into the holder, and the rolled portion 29 is stretched and mounted over the open end 5 of the holder 1 to lie within the channel 17 as shown in FIG. 2. The closed end 23 of the condom 21 lies close to the closed end 7 of the holder 1, and an air space 33 is formed between the flaccid unrolled portion 27 of the condom 21 and the inner surface 35 of the wall of the member 3.

In this position, the valve 15 is opened and air is sucked out of the space 33 by the mouth of the user through the opening 9 and the extension 11. As the space 33 is evacuated, the unrolled portion 27 of the condom 21 stretches and enlarges to come into contact with the inner surface 35 of the wall as shown in FIG. 3. The valve 15 is now closed. The holder 1 with the mounted, stretched condom 21, is now positioned over an erect penis 41. When in position, the valve 15 is opened, allowing air to rush into the holder through opening 9, and the unrolled portion 27 of the condom 21 collapses onto the penis 41 as shown in FIG. 4. The rolled portion 29 of the condom 21 is detached from the holder 1 and the holder is removed. The rolled portion 29 of the condom can be unrolled onto the lower part of the penis. It will be seen that the selective operation of the valve 15 allows a condom to be easily stretched and then donned on a penis.

Preferably the holder 1 is provided with a shield 45 that lies within the holder overlying the opening 9 as shown in FIG. 5. The shield 45 is spaced slightly from the wall, and passageways 47 are provided for air passing between the opening 9 and the interior of the holder 1. The shield 45 prevents the closed end 23 of the condom 21 from blocking the opening 9 as air is being evacuated from the space 33.

The holder 1 can be pleated as shown in FIG. 6. The pleats 47 are of the type that resist opening up from the closed position and also resist closing from the open position. The resistance allows the holder to remain in the open position or the closed position. These types of pleats are known. The pleats allow the holder to be stored in a minimum amount of space. The holder 1 can be made of different available packaging materials. It should be transparent, and preferably it would be made of acrylic.

The holder 1 can be sold with a condom already mounted thereon. However, the holder can be sold without the condom. The holder can be used many times with a fresh condom each time.

Figure 9:
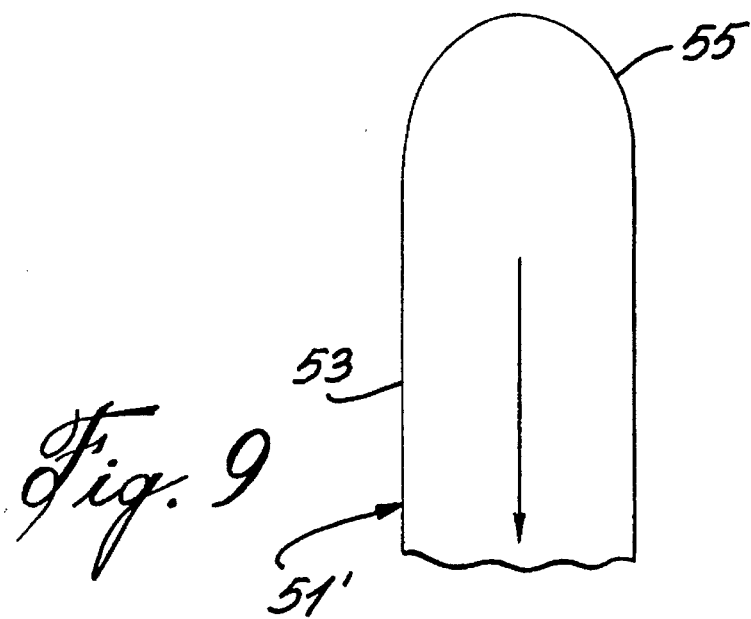
FIG. 9 is a view, similar to FIG. 7, showing the condom mounted on the holder and the adapter being withdrawn.

In another embodiment of the invention, as shown in FIG. 9, the holder can have closure means in the form of a seal instead of a valve. In this embodiment, the holder 1' has all the same elements as the holder shown in FIG. 1, except for the valve. As shown in FIG. 7, the holder 1' has a tubular extension 13' as before at the closed end 7' of the holder but the valve is omitted.

The condom can be manually mounted on this holder as before. Preferably, however, the condom is mounted on the holder with the aid of an adapter 51 as shown in FIG. 7. The adapter 51 comprises a member shaped like an erect penis with a shaft 53 and a rounded end 55. A channel or groove 54 is provided to allow air to be released when the condom is mounted to the adapter 51. The condom 21' is partly unrolled, and the unrolled portion 27' is placed on the adapter 51. The adapter 51 is moved into the holder 1' to position the condom within the holder. The rolled portion 29' of the condom 21' is then stretched off the adapter 51, and mounted onto the mounting means 17' on the outside of the holder 1' adjacent its open end 5' as shown in FIG. 8. Air evacuating means (not shown) are then connected to the extension 13' to withdraw air from within the holder. This causes the unrolled portion 27' of the condom to stretch and enlarge moving off the adapter 51 and against the inner surface 35' of the wall 11' of the holder. The air opening 9' is then closed with a frangible or removable seal 59, and the adapter 51 is removed as shown in FIG. 9. The stretched condom and holder form a condom unit 61 that can be packaged and sold. This condom unit 61 is used by unpackaging it, positioning the holder and thus the stretched condom over a penis and removing or breaking the seal 59. When the seal is broken, air rushes in and the condom collapses about the penis. The holder is detached from the condom and discarded or it may be reused as described above.

The above condom unit is particularly suited for an assembly line process of manufacture, particularly with using the adapter to help assemble it. The unit can be assembled with total or partial mechanical means with each step being carried out at a different work station.

If desired, the condom unit 61 can employ a pleated holder so that the unit can be collapsed for packaging, sale and/or storage. Also, the holder 1' can employ a shield the same as shield 45 shown in FIG. 5.

I claim:

1. A condom holder for use in applying a condom onto a penis comprising: a single-walled, tubular member having a closed end and an open end; the member sized to very loosely cover the upper half of an erect penis; mounting means on the outside of the member adjacent its open end for mounting the open end of a condom thereon with an unrolled portion of the condom located within the member; an air opening in the closed end of the condom to allow the passage of air in a space, formed between the unrolled portion of the condom and the interior surface of the member, and the atmosphere; and a two way valve with a mechanical shut-off means on the member for selectively first evacuating the air from said space causing the unrolled portion of the condom to stretch and come into contact with the interior surface of the member and expand for allowing air to enter the space and thus collapse the condom on the penis.

2. A holder as claimed in claim 1, including a shield within the holder at the closed end and overlying the air opening to prevent the tip of a condom from blocking the opening when evacuating the holder, the shield spaced a short distance from the closed end.

3. A holder as claimed in claim 1, wherein the valve comprises a frangible or removable seal that can be broken or removed at the time the holder is being used to apply a condom.

4. A holder as claimed in claim 1, wherein the member is pleated so that it can be collapsed for packaging after the air has been evacuated from the space and the valve is closed with the condom drawn against said interior surface.

5. A method of donning a condom using a condom holder, which holder comprises a tubular member having a closed end and an open end; condom mounting means outside the member adjacent its open end; an air opening in the closed end and closure means on the member for selectively closing the air outlet; the method comprising the steps of partially unrolling the condom and inserting the unrolled portion within the holder; mounting the rolled portion of the condom on the mounting means; withdrawing air from within the space between the holder and the condom through the air opening to cause the unrolled portion of the condom to stretch and enlarge; closing the air opening; positioning the holder and condom on a penis; opening the air opening to allow the unrolled portion of the condom to collapse onto the penis; removing the rolled portion of the condom from the holder and unrolling the remainder of the condom onto the penis.

6. A method as claimed in claim 5, wherein the air is evacuated in a factory and the air opening is closed with a frangible or removable seal that can be broken or removed at the point of use of the condom.

7. A method as claimed in claim 6, wherein the unit is collapsed at the factory after the air is evacuated so as to minimize packaging.

8. A method as claimed in claim 5, wherein the air is evacuated at the point of use of the condom by the mouth of the user and the air opening is closed by a valve in the member.

9. A condom application device comprising a single-walled tubular member having a closed end and an open end and an interior surface; an air passage at the closed end of the condom; mounting means on the outside of the member adjacent the open end for mounting a condom thereon; a condom installed in the member, the condom being partially unrolled with the unrolled portion positioned within the member and with the rolled portion being mounted on the mounting means; the unrolled portion being enlarged and stretched within the member against the interior surface by means of the air having been evacuated through the air passage; and a two-way valve with a mechanical shut-off on the member normally closing the air passage and for selectively opening the air passage to allow air to enter the member so that the stretched condom will collapse when it is required to apply the condom on a penis.

10. A condom application device as claimed in claim 9, wherein the valve comprises a frangible or removable seal that can be broken or removed at the point of use of the condom.

11. A condom unit as claimed in claim 10, wherein the holder is pleated so that the unit can be sold in a collapsed condition.

* * * * *